US008314235B2

(12) United States Patent
Dixit et al.

(10) Patent No.: US 8,314,235 B2
(45) Date of Patent: Nov. 20, 2012

(54) PROCESS FOR PREPARING VARENICLINE, VARENICLINE INTERMEDIATES, PHARMACEUTICALLY ACCEPTABLE SALTS THEREOF

(75) Inventors: Girish Dixit, Uttar Pradesh (IN); Krishnadatt Sharma, Mumbai (IN); Kundan Singh Shekhawat, Rajasthan (IN); Nitin Sharadchandra Pradhan, Maharashtra (IN)

(73) Assignee: Actavis Group PTC EHF (IS)

( * ) Notice: Subject to any disclaimer, the term of this patent is extended or adjusted under 35 U.S.C. 154(b) by 0 days.

(21) Appl. No.: 13/060,755

(22) PCT Filed: Aug. 31, 2009

(86) PCT No.: PCT/IB2009/007081
§ 371 (c)(1),
(2), (4) Date: May 25, 2011

(87) PCT Pub. No.: WO2010/023561
PCT Pub. Date: Mar. 4, 2010

(65) Prior Publication Data
US 2011/0224437 A1    Sep. 15, 2011

(30) Foreign Application Priority Data
Sep. 1, 2008  (IN) .......................... 2133/CHE/2008

(51) Int. Cl.
*C07D 241/40*  (2006.01)
(52) U.S. Cl. ..................................................... 544/343
(58) Field of Classification Search ................. 544/343
See application file for complete search history.

(56) References Cited

U.S. PATENT DOCUMENTS

| 6,410,550 | B1 | 6/2002 | Coe et al. |
| 6,605,610 | B1 * | 8/2003 | Coe et al. ........................ 514/250 |
| 6,890,927 | B2 | 5/2005 | Bogle et al. |
| 6,897,310 | B2 | 5/2005 | Coe et al. |
| 6,951,938 | B2 | 10/2005 | Coe et al. |
| 2002/0072524 | A1 | 6/2002 | Wadsworth et al. |

FOREIGN PATENT DOCUMENTS

| WO | 2004108725 A1 | 12/2004 |
| WO | 2008060487 A3 | 5/2008 |

OTHER PUBLICATIONS

Das, et al.; "An Efficient and Convenient Protocol for the Synthesis of Quinoxalines and Dihydropyrazines Via Cyclization-Oxidation Processes Using HCl)4 SiO2 as a Heterogeneous Recyclable Catalyst"; Tetrahedron Letters; 48; pp. 5371-5374; (2007).
International Search Report and Written Opinion; International Application No. PCT/IB2009/007081; International Filing Date Aug. 31, 2009; Date of Mailing Jan. 21, 2010; 14 pages.

* cited by examiner

*Primary Examiner* — Golam M M Shameem
*Assistant Examiner* — Karen Cheng
(74) *Attorney, Agent, or Firm* — Cantor Colburn LLP

(57) ABSTRACT

Provided herein is an improved, convenient, commercially viable and environmentally friendly process for the preparation of varenicline or a pharmaceutically acceptable salt thereof comprising reacting 1-(4,5-diamino-10-aza-tricyclo [$6.3.1.0^{2,7}$]dodeca-2(7),3,5-trien-10-yl)-2,2,2-trifluoro-ethanone with chloroacetaldehyde in the presence of an oxygen source. Provided further herein is an improved and industrially advantageous process for the preparation of 1-(4,5-diamino-10-aza-tricyclo[$6.3.1.0^{2,7}$]dodeca-2(7),3,5-trien-10-yl)-2,2,2-trifluoro-ethanone.

8 Claims, No Drawings

PROCESS FOR PREPARING VARENICLINE, VARENICLINE INTERMEDIATES, PHARMACEUTICALLY ACCEPTABLE SALTS THEREOF

CROSS-REFERENCE TO RELATED APPLICATIONS

This application is a 371 of PCT/IB2009/007081, filed Aug. 31, 2009, which claims the benefit of priority to Indian provisional application No. 2133/CHE/2008, filed on Sep. 1, 2008, under the provisions of 35 U.S.C. 119 and the International Convention for the protection of Industrial Property, which are incorporated herein by reference in their entirety.

FIELD OF THE DISCLOSURE

Disclosed herein is a convenient, commercially viable and environmentally friendly process for the preparation of varenicline or a pharmaceutically acceptable salt thereof. Disclosed further herein is an improved and industrially advantageous process for the preparation of a varenicline intermediate.

BACKGROUND OF THE INVENTION

Varenicline, 7,8,9,10-tetrahydro-6,10-methano-6H-pyrazino[2,3-h][3]benzazepine, is known to bind to neuronal nicotinic acetylcholine specific receptor sites and is useful in modulating cholinergic function. This compound is useful in the treatment of inflammatory bowel disease, irritable bowel syndrome, spastic dystonia, chronic pain, acute pain, vasoconstriction, anxiety, panic disorder, depression, cognitive dysfunction, drug/toxin-induced cognitive impairment (e.g., from alcohol, barbiturates, vitamin deficiencies, recreational drugs, lead, arsenic, mercury), particularly, nicotine dependency, addiction and withdrawal; including use in smoking cessation therapy. Varenicline is represented by the following structural formula:

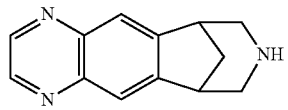

I and its first synthesis was disclosed in U.S. Pat. No. 6,410,550 (hereinafter referred to as the '550 patent). Varenicline is sold by Pfizer under the brand name CHANTIX™ to help adults quit smoking by blocking $\alpha_4\beta_2$ nicotinic acetylcholine receptor subtypes. It is orally administered as tablets containing 0.85 mg or 1.71 mg of varenicline tartrate equivalent to 0.5 mg or 1 mg of varenicline.

The '550 patent describes various processes for the preparation of aryl fused azapolycyclic compounds, including varenicline, and their pharmaceutically acceptable salts, combinations with other therapeutic agents, and methods of using such combinations in the treatment of neurogical and psychological disorders. Varenicline has been exemplified as a free base and a hydrochloride salt in the '550 patent.

U.S. Pat. No. 6,890,927 (hereinafter referred to as the '927 patent) discloses tartrate salts, including L-tartrate, D-tartrate, D,L-tartrate and meso-tartrate, of varenicline and their polymorphs, processes for their preparation, and pharmaceutical compositions thereof. The '927 patent further discloses various polymorphs of the varenicline L-tartrate salt, including two anhydrous polymorphs (Forms A & B) and a hydrate polymorph (Form C), and characterizes them by powder X-ray diffraction (P-XRD), X-ray crystal structure, solid state $^{13}$C NMR spectroscopy, and Differential Scanning calorimetry (DSC).

Varenicline tartrate, 7,8,9,10-tetrahydro-6,10-methano-6H-pyrazino[2,3-h][3]benzazepine, (2R,3R)-2,3-dihydroxybutanedioate (1:1), has a molecular weight of 361.35 Daltons, and a molecular formula of $C_{13}H_{13}N_3 \cdot C_4H_6O_6$. Varenicline tartrate is represented by the following structural formula:

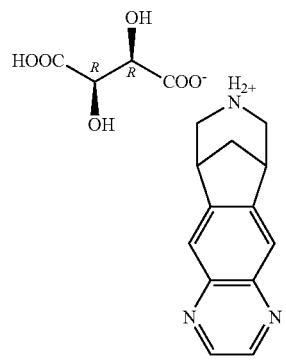

U.S. Pat. Nos. 6,897,310 and 6,951,938 describe a process for the preparation of aryl fused azapolycyclic compounds and their pharmaceutically acceptable salts in combination with another therapeutic agents and methods of using such combinations in the treatment of neurogical and psychological disorder. The '938 patent discloses the ring closure for making quinoxalines by reacting diamine compound with glyoxal or glyoxal derivatives in water or other polar solvents such as tetrahydrofuran, dimethylformamide or dimethylsulfoxide at a temperature of about 40° C. to about 100° C.

PCT publication WO2004/108725 describes a process for the preparation of substituted quinoxalines by cyclization of the corresponding diamine compound with 2,3-dihydroxy-1,4-dioxane.

PCT Publication WO 2008/060487 (hereinafter referred to as the '487 application) discloses crystal forms of intermediates used in the process for the preparation of varenicline tartrate including the varenicline free base. According to the '487 application, the varenicline free base exists in four crystalline forms (Form A, Form C, Form D and Form E).

The synthetic routes described in the above mentioned prior art suffers from disadvantages such as high cost of reagents, the use of pyrophoric and hazardous reagents, the use of additional reagents and low yields of product. Hence, these routes are not advisable for scale up operations.

A need remains for an improved and commercially viable process of preparing a substantially pure varenicline or a pharmaceutically acceptable salt thereof, to resolve the problems associated with the processes described in the prior art, and that will be suitable for large-scale preparation, in a shorter reaction time. Desirable process properties include less hazardous and environmentally friendly reagents, reduced cost, greater simplicity, increased product purity and increased yield of the product.

SUMMARY

The present inventors have surprisingly found that varenicline can be prepared in high purity and with high yield by condensing a protected diamino-10-aza-tricyclo compound with haloacetaldehyde in the presence or absence of an oxygen source in a suitable solvent to produce a protected triazatetracyclo compound, followed by deprotection. The novel process solves the drawbacks associated with the prior processes and is commercially viable for preparing varenicline.

In one embodiment, a process for the preparation of varenicline of formula I:

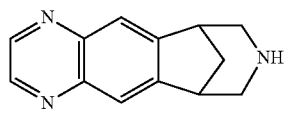

I or a pharmaceutically acceptable salt thereof comprises:
a) reacting a protected diaminoazatricyclo compound of formula III:

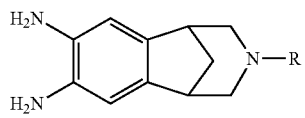

III wherein 'R' represents a nitrogen protecting group, with haloacetaldehyde compound of formula IV:

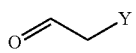

IV wherein 'Y' represents a halogen atom selected from the group consisting of F, Cl, Br and I; optionally in the presence of oxygen source, to provide a protected triazatetracyclo compound of formula II:

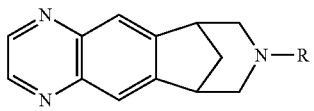

II wherein R is as defined in formula III; and
b) deprotecting the compound of formula II to provide pure varenicline of formula I, and optionally converting the varenicline obtained into a pharmaceutically acceptable salt thereof.

In one aspect, provided herein is an efficient, convenient, commercially viable and environment friendly process for the preparation of varenicline or a pharmaceutically acceptable salt thereof. Advantageously, the reagents used for the present invention are less hazardous and easier to handle at a commercial scale, and are also less expensive reagents than those used previously.

In another aspect, provided also herein is an improved, convenient, commercially viable process for the preparation of the protected diamino-10-aza-tricyclo intermediate.

DETAILED DESCRIPTION

According to one aspect, there is provided a process for the preparation of varenicline of formula I:

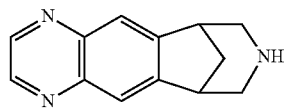

I or a pharmaceutically acceptable salt thereof, comprising:
a) reacting a protected diaminoazatricyclo compound of formula III:

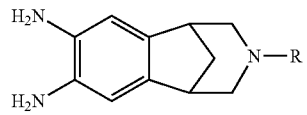

III wherein 'R' represents a nitrogen protecting group, with haloacetaldehyde compound of formula IV:

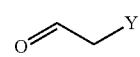

IV wherein 'Y' represents a halogen atom selected from the group consisting of F, Cl, Br and I; optionally in the presence of oxygen source, to provide a protected triazatetracyclo compound of formula II:

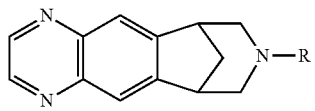

II wherein R is as defined in formula III; and
b) deprotecting the compound of formula II to provide pure varenicline of formula I and optionally converting the varenicline obtained in to a pharmaceutically acceptable salt thereof.

In one embodiment, the reaction in step-(a) is carried out in the presence of a solvent. The term solvent also includes mixtures of solvents.

Exemplary solvents employed in step-(a) include, but are not limited to, water, an alcohol, a chlorinated hydrocarbon, a ketone, a polar aprotic solvent, a nitrile, an ester, and mixtures thereof.

Specifically, the solvent is selected from the group consisting of water, methanol, ethanol, isopropyl alcohol, n-propanol, tert-butanol, n-butanol, methylene chloride, ethyl dichloride, chloroform, carbon tetrachloride, acetone, methyl isobutyl ketone, N,N-dimethylformamide, N,N-dimethylacetamide, dimethylsulfoxide, acetonitrile, propionitrile, ethyl acetate, isopropyl acetate, and mixtures thereof. More specifically, the solvent is selected from the group consisting of water, dimethylsulfoxide, N,N-dimethylformamide, dimethylacetamide, and mixtures thereof.

In one embodiment, the amount of solvent employed in the coupling reaction is about 5 volumes to about 25 volumes, and specifically about 7 volumes to about 15 volumes with respect to the diaminoazatricyclo compound of formula III.

Exemplary oxygen sources employed in step-(a) include, but are not limited to, lead monoxide, manganese dioxide, mercuric iodide, ceric ammonium nitrate, and the like, and combinations thereof. A specific oxygen source is lead monoxide.

The condensation reaction in step-(a) is carried out at a temperature of about 0° C. to the reflux temperature of the solvent used, specifically at a temperature of about 25° C. to the reflux temperature of the solvent used for at least 1 hour, and most specifically at the reflux temperature of the solvent used for about 2 hours to about 10 hours. The reaction mass may be quenched with water after completion of the reaction.

As used herein, "reflux temperature" means the temperature at which the solvent or solvent system refluxes or boils at atmospheric pressure.

Exemplary nitrogen protecting groups 'R' include, but are not limited to, acetyl, trifluoroacetyl, trichloroacetyl, pyrrolidinylmethyl, cumyl, benzhydryl, trityl, benzyloxycarbonyl (Cbz), 9-fluorenylmethyloxy carbonyl (Fmoc), benzyloxymethyl (BOM), pivaloyloxymethyl (POM), trichloroethoxycarbonyl (Troc), 1-adamantyloxycarbonyl (Adoc), allyl, allyloxycarbonyl, trimethylsilyl, tert.-butyldimethylsilyl, triethylsilyl (TES), triisopropylsilyl, trimethylsilylethoxymethyl (SEM), t-butoxycarbonyl (BOC), t-butyl, 1-methyl-1, 1-dimethylbenzyl, pyrridinyl and pivaloyl. Specific nitrogen protecting groups are trifluoroacetyl, trichloroacetyl, trichloroethoxycarbonyl, benzyloxycarbonyl, t-butoxycarbonyl, allyloxycarbonyl and pivaloyl. A most specific nitrogen protecting group is trifluoroacetyl.

In one embodiment, the halogen atom 'Y' in the compound of formula IV is Cl.

The reaction mass containing the protected triazatetracyclo compound of formula II obtained in step-(a) is optionally subjected to usual work up such as a washing, an extraction, a layer separation, an evaporation, a filtration, a pH adjustment or a combination thereof. The reaction mass may be used directly in the next step to produce varenicline of formula I, or the compound of formula II may be isolated and then used in the next step.

The removal of protecting groups in step-(b) can be achieved by conventional methods used in peptide chemistry and are described e.g. in the relevant chapters of standard reference works such as J. F. W. McOmie, "Protective Groups in Organic Chemistry", Plenum Press, London and New York 1973, in T. W. Greene and P. G. M. Wuts, "Protective Groups in Organic Synthesis", Third edition, Wiley, New York 1999, in "The Peptides"; Volume 3 (editors: E. Gross and J. Meienhofer), Academic Press, London and New York 1981.

In one embodiment, the deprotection in step-(b) is carried out by treating the protected triazatetracyclo compound of formula II with a base in a reaction inert solvent.

The base used for deprotection is an organic or inorganic base. Specific organic bases are triethyl amine, trimethylamine, N,N-diisopropylethylamine, N-methylmorpholine and N-methylpiperidine. Specific inorganic bases are ammonia, sodium hydroxide, calcium hydroxide, magnesium hydroxide, potassium hydroxide, lithium hydroxide, sodium carbonate, potassium carbonate, lithium carbonate, sodium tert-butoxide, sodium isopropoxide and potassium tert-butoxide. A most specific base is sodium hydroxide or potassium hydroxide.

Exemplary solvents used for deprotection in step-(b) include, but are not limited to, water, an alcohol, a chlorinated hydrocarbon, a ketone, a polar aprotic solvent, a nitrile, an ester, and mixtures thereof. In one embodiment, the solvent is selected from the group consisting of water, methanol, ethanol, isopropyl alcohol, acetone, and mixtures thereof.

The reaction mass containing the varenicline of formula I obtained in step-(b) is optionally subjected to usual work up such as a washing, an extraction, a layer separation, an evaporation, a filtration, a pH adjustment or a combination thereof, followed by isolation as solid from a suitable solvent by conventional methods such as cooling, seeding, partial removal of the solvent from the solution, by adding an anti-solvent to the solution, evaporation, vacuum drying, spray drying, freeze drying, or a combination thereof.

In one embodiment, the solvent used for isolating the pure varenicline is selected from the group consisting of water, methanol, ethanol, isopropyl alcohol, t-butanol, acetone, tetrahydrofuran, dioxane, diethyl ether, diisopropyl ether, monoglyme, diglyme, and mixtures thereof. A most specific solvent is diisopropyl ether.

In another embodiment, the isolation is carried out by cooling the solution at a temperature of below 30° C. for at least 30 minutes, specifically at about 0° C. to about 30° C. for about 1 hour to about 20 hours, and more specifically at about 0° C. to about 25° C. for about 2 hours to about 10 hours. The solid obtained is then recovered by techniques such as filtration, filtration under vacuum, decantation, centrifugation, or a combination thereof. In one embodiment, the solid is recovered by filtration employing a filtration media of, for example, a silica gel or celite.

The pure varenicline obtained by the process disclosed herein may be further dried in, for example, a Vacuum Tray Dryer, a Rotocon Vacuum Dryer, a Vacuum Paddle Dryer or a pilot plant Rota vapor, to further lower residual solvents. Drying can be carried out under reduced pressure until the residual solvent content reduces to the desired amount such as an amount that is within the limits given by the International Conference on Harmonization of Technical Requirements for Registration of Pharmaceuticals for Human Use ("ICH") guidelines.

In one embodiment, the drying is carried out at atmospheric pressure or reduced pressures, such as below about 200 mm Hg, or below about 50 mm Hg, at temperatures such as about 35° C. to about 70° C. The drying can be carried out for any desired time period that achieves the desired result, such as about 1 to 20 hours. Drying may also be carried out for shorter or longer periods of time depending on the product specifications. Temperatures and pressures will be chosen based on the volatility of the solvent being used and the foregoing should be considered as only a general guidance. Drying can be suitably carried out in a tray dryer, vacuum oven, air oven, or using a fluidized bed drier, spin flash dryer, flash dryer and the like. Drying equipment selection is well within the ordinary skill in the art.

The varenicline of formula I obtained by the process disclosed herein has a purity (measured by High Performance Liquid Chromatography, hereinafter referred to as 'HPLC') greater than about 98%, specifically greater than about 99%, more specifically greater than about 99.5%, and still more specifically greater than about 99.9%. For example, the purity of the varenicline can be about 99% to about 99.95%, or about 99.5% to about 99.99%.

Pharmaceutically acceptable salts of varenicline can be prepared in high purity by using the substantially pure varenicline obtained by the methods disclosed herein, by known methods.

Exemplary pharmaceutically acceptable salts of varenicline are obtained from organic and inorganic acids include hydrochloric acid, hydrobromic acid, sulfuric acid, phosphoric acid, tartaric acid, derivatives of tartaric acid, fumaric acid, maleic acid, oxalic acid, acetic acid, propionic acid, succinic acid, mandelic acid, citric acid, and more preferable salt being varenicline tartrate.

According to another aspect, there is provided a process for the preparation of the protected diaminoazotricyclo compound of formula III:
a) oxidizing 1,2,3,4-tetrahydro-1,4-methanonaphthalene-2,3-diol of formula X:

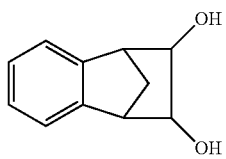

X in the presence of an oxidizing agent in a solvent, optionally in the presence of a phase transfer catalyst, to provide indane-1,3-dicarbaldehyde of formula IX:

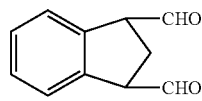

IX b) reacting the compound of formula IX with benzyl amine in the presence of a reducing agent, optionally in the presence of a Lewis acid, in a solvent to provide 10-benzyl-10-azatricyclo[6.3.1.0$^{2.7}$]-dodeca-2(7),3,5-triene of formula VIII:

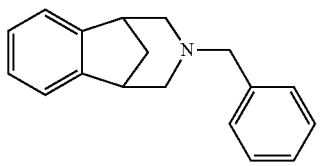

VIII c) hydrogenating the compound of formula VIII using a hydrogenation catalyst in the presence of a hydrogen source in a solvent to provide 10-aza-tricyclo[6.3.1.0$^{2.7}$]-dodeca-2(7),3,5-triene of formula VII:

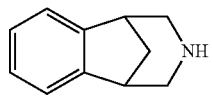

VII or an acid addition salt thereof, preferably hydrochloride salt, wherein the hydrogen source is a formate salt;

d) protecting the compound of formula VII with a nitrogen protecting group 'R' to provide a protected compound of formula VI:

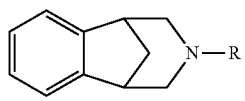

VI wherein 'R' represents a nitrogen protecting group;

e) nitrating the compound of formula VI in the presence of a mixture of nitric acid and sulfuric acid in a solvent, to provide a dinitro compound of formula V:

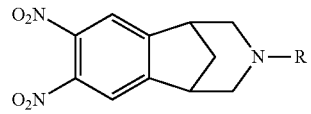

V wherein R is as defined in formula VI; and f) hydrogenating the compound of formula V using a hydrogenation catalyst in the presence of a hydrogen source in a solvent to provide the protected diaminoazatricyclo compound of formula III, wherein the hydrogen source is a formate salt.

Exemplary nitrogen protecting group 'R' used in the compounds of formulae III, V and VI are selected from the group as described above. A most specific nitrogen protecting group is trifluoroacetyl.

These groups may be added or removed by conventional methods used in peptide chemistry as described above.

Exemplary solvents used in step-(a) include, but are not limited to, water, an alcohol, a ketone, a cyclic ether, an aliphatic ether, a hydrocarbon, a chlorinated hydrocarbon, a nitrile, an ester, and mixtures thereof.

Specifically, the solvent is selected from the group consisting of water, methanol, ethanol, isopropyl alcohol, n-propanol, tert-butanol, n-butanol, amyl alcohol, hexanol, acetone, methyl isobutyl ketone, tetrahydrofuran, dioxane, diethyl ether, diisopropyl ether, monoglyme, diglyme, acetonitrile, ethyl acetate, isopropyl acetate, n-pentane, n-hexane, n-heptane, cyclohexane, toluene, xylene, methylene chloride, ethyl dichloride, chloroform, carbon tetrachloride, and mixtures thereof; more specifically, the solvent is selected from the group consisting of water, n-hexane, n-heptane, cyclohexane, toluene, xylene, methylene chloride, and mixtures thereof; and a most specific solvent is a mixture of water and methylene chloride.

Exemplary oxidizing agents used in step-(a) include, but are not limited to, sodium periodate, sodium chlorate, sodium hypochlorite, collins reagent, barium permanganate, 2,2,6,6-tetramethylpiperidinyloxy (TEMPO), iodine/$K_2CO_3$, N-chlorosuccinimide/dimethylsulfide, ceric ammonium nitrate, and the like. A specific oxidizing agent is sodium periodate. Collins reagent is the complex of chromium (VI) oxide with pyridine in dichloromethane. It is used to selectively oxidize primary alcohols to the aldehyde, and will tolerate many other functional groups within the molecule. It can be used as an alternative to the Jones reagent and pyridinium chlorochromate when oxidising secondary alcohols to ketones. Moreover, the Collins reagent is especially useful for oxidations of acid sensitive compounds.

In one embodiment, the oxidizing agent is used in a molar ratio of about 1 to 5 moles, specifically about 1 to 2 moles, per 1 mole of the 1,2,3,4-tetrahydro-1,4-methanonaphthalene-2,3-diol of formula X in order to ensure a proper course of the reaction.

The reaction in step-(a) is carried out at a temperature of below about 50° C., specifically at a temperature of about 0° C. to about 40° C. for at least 30 minutes, and more specifically at about 10° C. to about 40° C. from about 1 hour to about 5 hours.

In one embodiment, the oxidation in step-(a) is carried out in the presence of a phase transfer catalyst. A "phase transfer catalyst" refers to a catalyst or agent which is added to a reaction mixture of components, to transfer one or more of the reacting components to a location where it can conveniently and rapidly react with another reacting component.

Exemplary phase transfer catalysts for use herein include, but are not limited to, quaternary ammonium salts substituted with a residue such as a straight or branched alkyl group having 1 to about 18 carbon atoms, phenyl lower alkyl group including a straight or branched alkyl group having 1 to 6 carbon atoms which is substituted by an aryl group and phenyl group, e.g., tetrabutylammonium chloride, tetrabutylammonium bromide, tetrabutylammonium fluoride, tetrabutylammonium iodide, tetrabutylammonium hydroxide, tetrabutylammonium hydrogen sulfate, tributylmethylammonium chloride, tributylbenzylammonium chloride, tetraethylammonium chloride, tetramethylammonium chloride, tetrapentylammonium chloride, tetrapentylammonium bromide, tetrahexyl ammonium chloride, benzyldimethyloctylammonium chloride, methyltrihexylammonium chloride, benzylmethyloctadecanylammonium chloride, methyltridecanylammonium chloride, benzyltripropylammonium chloride, benzyltriethyl ammonium chloride, phenyltriethylammonium chloride and the like; phosphonium salts substituted with a residue such as a straight or branched alkyl group having 1 to about 18 carbon atoms, e.g., tetrabutylphosphonium chloride and the like; and pyridinium salts substituted with a straight or branched alkyl group having 1 to about 18 carbon atoms, e.g., 1-dodecanylpyridinium chloride and the like.

Specific phase transfer catalysts are tetrabutylammonium bromide, tetrabutylphosphonium bromide, tetrabutylammonium chloride, tetrabutylphosphonium chloride, benzyltriethylammonium chloride, tetrabutylammonium hydrogen sulfate; and more specifically benzyltriethylammonium chloride or tetrabutylammonium bromide.

In one embodiment, the amount of the phase transfer catalyst employed is 0.5% w/w to about 10% w/w, and specifically from about 5% w/w to about 10% w/w.

The reaction mass containing the indane-1,3-dicarbaldehyde of formula IX obtained in step-(a) is optionally subjected to usual work up such as a washing, an extraction, a layer separation, an evaporation, a filtration, a pH adjustment or a combination thereof. The reaction mass may be used directly in the next step to produce 10-benzyl-10-aza-tricyclo[6.3.1.0$^{2.7}$]-dodeca-2(7),3,5-triene of formula VIII, or the compound of formula IX may be isolated and then used in the next step.

Exemplary solvents used in step-(b) include, but are not limited to, a cyclic ether, an aliphatic ether, a hydrocarbon, a chlorinated hydrocarbon, a nitrile, an ester and the like, and mixtures thereof.

Specifically, the solvent is selected from the group consisting of tetrahydrofuran, dioxane, diethyl ether, diisopropyl ether, monoglyme, diglyme, acetonitrile, ethyl acetate, isopropyl acetate, n-pentane, n-hexane, n-heptane, cyclohexane, toluene, xylene, methylene chloride, ethyl dichloride, chloroform, carbon tetrachloride, and mixtures thereof; and more specifically, the solvent is selected from the group consisting of methylene chloride, toluene, and mixtures thereof.

The reducing agent used in step-(b) is selected from the group consisting of sodium borohydride, sodium cyanoborohydride, lithium aluminium hydride, diisobutyl aluminium hydride, borane and its derivatives. A specific reducing agent is sodium cyanoborohydride.

The Lewis acid used in step-(b) is selected from the group consisting of aluminium chloride, calcium chloride, boron triflouride and zinc chloride. A specific Lewis acid is aluminium chloride.

In one embodiment, the reducing agent is used in a molar ratio of about 1 to 5 moles, specifically about 2.5 to 3.5 moles, per 1 mole of the compound of formula IX in order to ensure a proper course of the reaction.

The reaction in step-(b) is carried out at a temperature of below about 50° C., specifically at a temperature of about 0° C. to about 40° C. for at least 30 minutes, and more specifically at about 10° C. to about 40° C. from about 1 hour to about 5 hours.

The reaction mass containing the 10-benzyl-10-aza-tricyclo[6.3.1.0$^{2.7}$]-dodeca-2(7),3,5-triene of formula VIII obtained in step-(b) is optionally subjected to usual work up such as a washing, an extraction, a layer separation, an evaporation, a filtration, a pH adjustment or a combination thereof. The reaction mass may be used directly in the next step to produce 10-aza-tricyclo[6.3.1.0$^{2.7}$]-dodeca-2(7),3,5-triene of formula VII, or the compound of formula VIII may be isolated and then used in the next step.

Exemplary solvents used in step-(c) include, but are not limited to, water, an alcohol, a ketone, a nitrile, an ester, tetrahydrofuran, N,N-dimethylformamide, N,N-dimethylacetamide, dimethylsulfoxide, and mixtures thereof.

Specifically, the solvent is selected from the group consisting of water, methanol, ethanol, isopropyl alcohol, n-propanol, tert-butanol, n-butanol, amyl alcohol, hexanol, acetone, methyl isobutyl ketone, tetrahydrofuran, acetonitrile, ethyl acetate, isopropyl acetate, N,N-dimethylformamide, N,N-dimethylacetamide, dimethylsulfoxide, and mixtures thereof; and a most specific solvent is methanol.

Exemplary hydrogenation catalysts used in step-(c) include, but are not limited to, platinum catalysts such as platinum plate, platinum sponge, platinum black, colloidal platinum, platinum oxide, platinum wire and the like; palladium catalysts such as palladium sponge, palladium black, palladium oxide, palladium on carbon, palladium hydroxide on carbon, colloidal palladium, palladium on barium sulfate, palladium on barium carbonate and the like; and nickel catalysts such as reduced nickel, nickel oxide, Raney nickel and the like. A specific hydrogenation catalyst is palladium hydroxide.

Exemplary formate salts used in step-(c) include, but are not limited to, ammonium formate, and an alkali metal salt of formic acid such as sodium formate and potassium formate. A specific formate salt is ammonium formate.

The reaction in step-(c) is carried out at a temperature of about 0° C. to the reflux temperature of the solvent used, specifically at a temperature of about 10° C. to the reflux temperature of the solvent used, more specifically at a temperature of about 40° C. to the reflux temperature of the solvent used for at least 20 minutes, and most specifically at the reflux temperature of the solvent used for about 30 minutes to about 5 hours.

The reaction mass containing the 10-aza-tricyclo[6.3.1.0$^{2.7}$]-dodeca-2(7),3,5-triene of formula VII obtained in step-(c) is optionally subjected to usual work up as described above. The reaction mass may be used directly in the next step to produce compound of formula VI, or the compound of formula VII may be isolated and then used in the next step, or the compound of formula VII may be converted into its acid addition salt followed by isolation and then used in the next step. In one embodiment, the compound of formula VII is converted into its acid addition salt by reaction with an acid in a solvent followed by isolation of an acid addition salt of the compound of formula VII as solid.

The acid addition salts are derived from a therapeutically acceptable acid such as hydrochloric acid, hydrobromic acid, sulfuric acid, nitric acid, oxalic acid, acetic acid, propionic acid and, phosphoric acid, succinic acid, maleic acid, fumaric acid, citric acid, glutaric acid, citraconic acid, glutaconic acid, tartaric acid, di-p-toluoyl-L-(+)-tartrate, malic acid, and ascorbic acid. A specific acid addition salt of the compound of formula VII is hydrochloride.

The treatment of the compound of formula VII with acid is carried out in a solvent selected from the group consisting of a chlorinated solvent, a hydrocarbon solvent, an ether solvent, an alcoholic solvent, a ketonic solvent, an ester solvents, and mixtures thereof.

Nitrogen protecting groups 'R' as used in step-(d) are described above.

Exemplary solvents used in step-(e) include, but are not limited to, a cyclic ether, an aliphatic ether, a hydrocarbon, a chlorinated hydrocarbon, a nitrile, an ester, and mixtures thereof.

Specifically, the solvent is selected from the group consisting of tetrahydrofuran, dioxane, diethyl ether, diisopropyl ether, monoglyme, diglyme, acetonitrile, ethyl acetate, isopropyl acetate, n-pentane, n-hexane, n-heptane, cyclohexane, toluene, xylene, methylene chloride, ethyl dichloride, chloroform, carbon tetrachloride, and mixtures thereof; and more specifically, the solvent is selected from the group consisting of methylene chloride, toluene, and mixtures thereof.

In one embodiment, the sulfuric acid employed in step-(e) is in the form of concentrated sulfuric acid.

In another embodiment, the nitric acid employed in step-(e) is in the form of concentrated nitric acid, specifically 95% concentrated nitric acid and more specifically 100% concentrated nitric acid. In one embodiment, the nitric acid is fuming nitric acid.

The nitration reaction in step-(e) is carried out at a temperature below 40° C. for about 3 hours to about 20 hours, and specifically at about 0° C. to about 30° C. for about 4 hours to about 10 hours.

The reaction mass containing the dinitro compound of formula V obtained in step-(e) is optionally subjected to usual work as described above. The reaction mass may be used directly in the next step to produce diamine compound of formula III, or the compound of formula V may be isolated and then used in the next step.

The isolation of the compound of formula V is performed from a suitable solvent by conventional methods such as cooling, seeding, partial removal of the solvent from the solution, by adding an anti-solvent to the solution, evaporation, vacuum drying, spray drying, freeze drying, or a combination thereof.

In one embodiment, the solvent used for isolating the pure compound of formula V is selected from the group consisting of water, methanol, ethanol, isopropyl alcohol, t-butanol, acetone, methylene chloride, and mixtures thereof. Most specific solvents are water, methanol and mixtures thereof.

Exemplary solvents used in step-(f) include, but are not limited to, water, an alcohol, a ketone, a nitrile, an ester, tetrahydrofuran, N,N-dimethylformamide, N,N-dimethylacetamide, dimethylsulfoxide, and mixtures thereof.

Specifically, the solvent is selected from the group consisting of water, methanol, ethanol, isopropyl alcohol, n-propanol, tert-butanol, n-butanol, amyl alcohol, hexanol, acetone, methyl isobutyl ketone, tetrahydrofuran, acetonitrile, ethyl acetate, isopropyl acetate, N,N-dimethylformamide, N,N-dimethylacetamide, dimethylsulfoxide, and mixtures thereof; and a most specific solvent is methanol.

The hydrogenation catalyst used in step-(f) is selected from the group as described above. A specific hydrogenation catalyst is palladium hydroxide.

The formate salt used in step-(f) is selected from the group as described above. A specific formate salt is ammonium formate.

The reaction in step-(f) is carried out at a temperature of about 0° C. to the reflux temperature of the solvent used, specifically at a temperature of about 10° C. to the reflux temperature of the solvent used, more specifically at a temperature of about 40° C. to the reflux temperature of the solvent used for at least 20 minutes, and most specifically at the reflux temperature of the solvent used for about 30 minutes to about 5 hours.

The reaction mass containing the diaminoazatricyclo compound of formula III obtained in step-(f) is optionally subjected to usual work up such as a washing, an extraction, a layer separation, an evaporation, a filtration, a pH adjustment or a combination thereof, followed by isolation as solid from a suitable solvent by conventional methods such as cooling, seeding, partial removal of the solvent from the solution, by adding an anti-solvent to the solution, evaporation, vacuum drying, spray drying, freeze drying, or a combination thereof.

In one embodiment, the solvent used for isolating the pure diaminoazatricyclo compound of formula III is selected from the group consisting of water, methanol, ethanol, isopropyl alcohol, t-butanol, acetone, tetrahydrofuran, dioxane, diethyl ether, diisopropyl ether, monoglyme, diglyme, and mixtures thereof. A most specific solvent is diisopropyl ether.

The total purity of the diaminoazatricyclo compound of formula III obtained by the process disclosed herein is greater than about 98%, specifically greater than about 99%, and more specifically greater than about 99.5% as measured by HPLC.

The following examples are given for the purpose of illustrating the present invention and should not be considered as limitation on the scope or spirit of the invention.

EXAMPLES

Example 1

Preparation of 10-Benzyl-10-aza-tricyclo[$6.3.1.0^{2.7}$]dodeca-2(7),3,5-triene 1,2,3,4-Tetrahydro-1,4-methanonaphthalene-2,3-diol (100 g) was stirred in a mixture of water (2600 ml) and methylene chloride (1040 ml) under nitrogen at 10° C. This step was followed by the addition of sodium periodate (127.6 g) and triethylbenzyl ammonium chloride (10 g). The resulting mixture was stirred for 1 hour followed by aqueous/organic layer separation. The aqueous layer was extracted with methylene chloride (500 ml). The organic layer was washed with water (4×1000 ml, or until no reaction to starch iodide was observed in the aqueous wash) and then dried over sodium sulfate. Benzyl amine (63.86 g) was added to the resulting organic layer, the mixture was stirred for 1 minute at 25-30° C., and then immediately added to the suspension of sodiumcyanoborohydride (114.25 g) in methylene chloride (2000 ml) at 0° C. in another reaction flask. The resulting orange mixture was warmed to 25-30° C. and stirred for 30 minutes to 1 hour. The reaction mass was quenched by adding saturated sodium carbonate solution (1000 ml) and stirred for 1 hour (pH: 9). The layers were separated and the aqueous layer was extracted with methylene chloride (500 ml). The organic layer was washed with saturated aqueous sodium chloride solution (2×600 ml) and dried over sodium sulfate followed by evaporation to afford a red oil. This oil was dissolved in a minimum of diethyl ether and filtered through a silica pad (3×4 inch) eluting with a mixture of 1000 ml of 15% ethyl acetate and 75% hexane solution to remove baseline red color. The resulting mass was concentrated under vacuum at 40-45° C. to yield 95 g of 10-benzyl-10-aza-tricyclo[6.3.1.0$^{2.7}$]dodeca-2(7),3,5-triene as yellow oil (Purity by HPLC: 99%).

Example 2

Preparation of 10-Aza-tricyclo[6.3.1.0$^{2.7}$]dodeca-2(7),3,5-triene hydrochloride salt 10-Benzyl-10-aza-tricyclo[6.3.1.0$^{2.7}$]dodeca-2(7),3,5-triene (94 g), ammonium formate (357 g) and 20% palladium hydroxide (7.5 g) were combined in methanol (1175 ml) and refluxed under nitrogen atmosphere for 30 minutes. The reaction mixture was cooled to 25° C. and filtered through a celite pad which was rinsed with methanol. The filtrate was concentrated and the resulted residue was treated with a saturated aqueous sodium carbonate solution (940 ml) and the resulting mass was extracted with methylene chloride (940 ml). The two layers were separated and the aqueous layer was extracted with methylene chloride (500 ml). The organic layer was washed with saturated aqueous sodium chloride solution (940 ml), dried over sodium sulfate and concentrated. The residue was treated with ethyl acetate (94 ml) and cooled to 0-5° C. Cooling was followed by the addition of hydrochloride in ethyl acetate (150 ml) at 0-5° C. and adjusting the pH to 1-2. The suspension was stirred at 0-5° C. for 1 hour and the resulting white crystals were collected by filtration to produce 64 g of 10-aza-tricyclo[6.3.1.0$^{2.7}$]dodeca-2(7),3,5-triene hydrochloride salt (Purity by HPLC: 99.68%).

Example 3

Preparation of 1-(10-Aza-tricyclo[6.3.1.0$^{2.7}$]dodeca-2(7),3,5-trien-10-yl)-2,2,2-trifluoro-ethanone 10-Aza-tricyclo[6.3.1.0$^{2.7}$]dodeca-2(7),3,5-triene hydrochloride salt (60 g) was stirred in methylene chloride (600 ml) at 25-30° C., the mixture was cooled to 0° C., and then treated with pyridine (61.68 g), followed by the addition of trifluoroacetic anhydride (TFAA) (81.39 g) over 10 minutes. Aqueous hydrochloric acid solution (600 ml) was added to the resulting mass followed by the separation of layers. The aqueous layer was extracted with methylene chloride (2×300 ml) and the combined organic layer was washed with aqueous hydrochloric acid solution (300 ml), water (2×600 ml) and saturated aqueous sodium bicarbonate solution (600 ml). The resulting solution was dried over sodium sulfate followed by concentration under vacuum at below 40° C. to afford a clear oil which was then crystallized to give 66 g of 1-(10-aza-tricyclo[6.3.1.0$^{2.7}$]dodeca-2(7),3,5-trien-10-yl)-2,2,2-trifluoro-ethanone as white needles (Purity by HPLC: 99.33%).

Example 4

Preparation of 1-(4,5-Dinitro-10-aza-tricyclo[6.3.1.0$^{2.7}$]dodeca-2(7),3,5-trien-10-yl)-2,2,2-trifluoro-ethanone Fuming nitric acid (39 g) was slowly added to a solution concentrated sulfuric acid (126.17 g) in methylene chloride (450 ml) followed by stirring at 0° C. to generate a white precipitate. This step was followed by drop wise addition of a solution of 1-(10-aza-tricyclo[6.3.1.0$^{2.7}$]dodeca-2(7),3,5-trien-10-yl)-2,2,2-trifluoro-ethanone (65 g) in methylene chloride (100 ml) through an addition funnel over 30 minutes. The reaction mixture was stirred for 2 hours 30 minutes at 0° C. and then stirred for 4 hours at 25-30° C. The resulting mass was poured into a vigorously stirred mixture of water (650 ml) at 15-20° C. The resulting layers were separated and the aqueous layer was extracted with methylene chloride (1×325 ml). The organic layers were combined and washed with water (3×650 ml) and then dried over sodium sulfate and concentrated to afford a solid. The resulting solid was slurried with methanol (325 ml), filtered and dried to yield 60 g of 1-(4,5-dinitro-10-aza-tricyclo[6.3.1.0$^{2.7}$]dodeca-2(7),3,5-trien-10-yl)-2,2,2-trifluoro-ethanone as off-white solid (Purity by HPLC: 99.5%).

Example 5

Preparation of 1-(4,5-Diamino-10-aza-tricyclo[6.3.1.0$^{2.7}$]dodeca-2(7),3,5-trien-10-yl)-2,2,2-trifluoro-ethanone 1-(4,5-Dinitro-10-aza-tricyclo[6.3.1.0$^{2.7}$]dodeca-2(7),3,5-trien-10-yl)-2,2,2-trifluoro-ethanone (40 g), ammonium formate (114.28 g) and 20% palladium hydroxide (4 g) were combined in methanol (400 ml) and refluxed for 30 minutes under a nitrogen atmosphere. The reaction mixture was cooled to 25° C. and filtered through a celite pad which was rinsed with methanol. The filtrate was concentrated and the product was extracted with methylene chloride (200 ml) and water (200 ml). The resulting two layers were extracted with methylene chloride (200 ml). The organic layer was washed with saturated aqueous sodium chloride solution (200 ml), dried over sodium sulfate and then concentrated. The residue was crystallized with diisopropyl ether (400 ml) followed by filtration to yield 13 g of 1-(4,5-diamino-10-aza-tricyclo[6.3.1.0$^{2.7}$]dodeca-2(7),3,5-trien-10-yl)-2,2,2-trifluoro-ethanone as pink crystals (Purity by HPLC: 99%).

Example 6

PREPARATION OF 1-(5,8,14-TRIAZATETRACYCLO[10.3.1.0$^{2.11}$.0$^{4.9}$]HEXADECA-2(11),3,5,7,9-PENTAENE)-2,2,2-TRIFLUORO-ETHANONE 1-(4,5-Diamino-10-aza-tricyclo[6.3.1.0$^{2.7}$]dodeca-2(7),3,5-trien-10-yl)-2,2,2-trifluoro-ethanone (1 g), 50% solution of chloroacetaldehyde (0.27 g) in water and lead monoxide (0.39 g) were heated in 20% aqueous dimethyl sulfoxide (80:20, dimethyl sulfoxide:water) (17 ml) at 60° C. The reaction mixture was stirred at 60° C. for 30 minutes. A 50% solution of chloroacetaldehyde (0.13 g) in water was added to the reaction mixture and then heated to 90° C. The reaction mixture was stirred for 30 minutes at 90° C. and followed by the addition of 50% solution of chloroacetaldehyde (0.15 g) in water at 90° C. The reaction mixture was stirred for 4-5 hours at 90-95° C. The resulting mass was cooled to 25-30° C. followed by the addition of water (34 ml). The unreacted lead monoxide was filtered and washed with water (34 ml). The filtrate was extracted with methylene chloride (5×25 ml) at 25-30° C. All the organic layers were combined and washed with 1N hydrochloric acid (3×25 ml). The organic layer was dried over sodium sulfate and charcoalized. The methylene chloride layer was concentrated under vacuum at below 45° C. followed by recrystallization in isopropyl alcohol to yield 0.6 g of 1-(5,8,14-triazatetracyclo[10.3.1.0$^{2.11}$.0$^{4.9}$]hexadeca-2(11),3,5,7,9-pentaene)-2,2,2-trifluoro-ethanone (Purity by HPLC: 99.88%).

Example 7

Preparation of 7,8,9,10-Tetrahydro-6,10-methano-6H-pyrazino[2,3-h][3]benzazepine (Varenicline)

1-(5,8,14-Triazatetracyclo[10.3.1.0$^{2.11}$.0$^{4.9}$]hexadeca-2(11),3,5,7,9-pentaene)-2,2,2-trifluoro-ethanone (100 g) was slurried in methanol (1000 ml) followed by treatment with sodium hydroxide (26 g) in water (50 ml). The mixture was heated for 1 hour at 40-45° C., the resulting mass concentrated under vacuum at below 45° C. followed by treatment with water (500 ml) and then extracted with methylene chloride (2×1000 ml). The organic layer was washed with water (1000 ml) and then dried over anhydrous sodium sulfate. Methylene dichloride was distilled out under vacuum followed by crystallization in diisopropyl ether. The brownish color solid obtained was dried at 50-55° C. to give 60 g of varenicline free base (Purity by HPLC: 99.8%).

Example 8

Preparation of 7,8,9,10-Tetrahydro-6,10-methano-6H-pyrazino[2,3-h][3]benzazepine, (2R,3R)-2,3-dihydroxybutanedioate (1:1) (Varenicline tartrate)

7,8,9,10-Tetrahydro-6,10-methano-6H-pyrazino-[2,3-h][3]benzazepine (50 g) was dissolved in methanol (375 ml) and the solution was added to a solution of tartaric acid (39.31 g) dissolved in methanol (375 ml) at 20-25° C. The suspension was stirred for 1 hour 30 minutes at 20-25° C. followed by filtration of the solid and then drying to yield 82 g of varenicline tartrate (Purity by HPLC: 99.9%).

We claim:

1. A process for the preparation of varenicline of formula I:

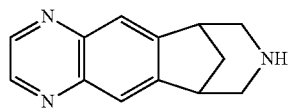

I or a pharmaceutically acceptable salt thereof; comprising:
a) reacting a protected diaminoazatricyclo compound of formula III:

III wherein 'R' represents a nitrogen protecting group, with haloacetaldehyde compound of formula IV:

IV wherein 'Y' represents a halogen atom selected from the group consisting of F, Cl, Br and I; in the presence of an oxygen source selected from the group consisting of lead monoxide, manganese dioxide, mercuric iodide and ceric ammonium nitrate, to provide a protected triazatetracyclo compound of formula II:

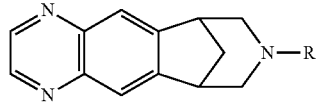

II wherein R is as defined in formula III;
b) deprotecting the compound of formula II, and
c) optionally converting the varenicline obtained into a pharmaceutically acceptable salt thereof.

2. The process of claim 1, wherein the reaction in step-(a) is carried out in the presence of a solvent selected from the group consisting of water, methanol, ethanol, isopropyl alcohol, n-propanol, tert-butanol, n-butanol, methylene chloride, ethyl dichloride, chloroform, carbon tetrachloride, acetone, methyl isobutyl ketone, N,N-dimethylformamide, N,N-dimethylacetamide, dimethylsulfoxide, acetonitrile, propionitrile, ethyl acetate, isopropyl acetate, and mixtures thereof.

3. The process of claim 1, wherein the condensation reaction in step-(a) is carried out at a temperature of about 0° C. to the reflux temperature of the solvent used wherein the varenicline of formula I obtained in step-(b) is isolated from a solvent by cooling, seeding, partial removal of the solvent from the solution, by adding an anti-solvent to the solution, evaporation, vacuum drying, spray drying, freeze drying, or a combination thereof, and wherein the solvent used for isolation is selected from the group consisting of water, methanol, ethanol, isopropyl alcohol, t-butanol, acetone, tetrahydrofuran, dioxane, diethyl ether, diisopropyl ether, monoglyme, diglyme, and mixtures thereof; and wherein the pharmaceutically acceptable salt of varenicline is a hydrochloride salt, a hydrobromide salt, a sulfate salt, a phosphate salt, a tartrate salt, a fumarate salt, a maleate salt, an oxalate salt, an acetate, a propionate salt, a succinate salt, a citrate salt, or a mandelate salt.

4. The process of claim 3, wherein the reaction is carried out at the reflux temperature of the solvent used for about 2 hours to about 10 hours.

5. The process of claim 1, wherein the nitrogen protecting group 'R' in the compounds of formulae II and III is selected from the group consisting of acetyl, trifluoroacetyl, trichloroacetyl, pyrrolidinylmethyl, cumyl, benzhydryl, trityl, benzyloxycarbonyl (Cbz), 9-fluorenylmethyloxy carbonyl (Fmoc), benzyloxymethyl (BOM), pivaloyloxymethyl (POM), trichloroethxoycarbonyl (Troc), 1-adamantyloxycarbonyl (Adoc), allyl, allyloxycarbonyl, trimethylsilyl, tert.-butyldimethylsilyl, triethylsilyl (TES), triisopropylsilyl, trimethylsilylethoxymethyl (SEM), t-butoxycarbonyl (BOC), t-butyl, 1-methyl-1,1-dimethylbenzyl, pyrridinyl and pivaloyl; and wherein the halogen atom 'Y' in the compound of formula IV is Cl.

6. The process of claim 5, wherein the nitrogen protecting group 'R' is trifluoroacetyl or t-butoxycarbonyl.

7. The process of claim 1, wherein the pharmaceutically acceptable salt of varenicline is a hydrochloride salt, a hydrobromide salt, a sulfate salt, a phosphate salt, a tartrate salt, a fumarate salt, a maleate salt, an oxalate salt, an acetate, a propionate salt, a succinate salt, a citrate salt, or a mandelate salt.

8. The process of claim 1, wherein the solvent used for isolation is selected from the group consisting of water, methanol, ethanol, isopropyl alcohol, t-butanol, acetone, tetrahydrofuran, dioxane, diethyl ether, diisopropyl ether, monoglyme, diglyme, and mixtures thereof.

* * * * *